United States Patent [19]

Child et al.

[11] Patent Number: 4,696,936

[45] Date of Patent: Sep. 29, 1987

[54] 3,6-BIS (SUBSTITUTED) ACRIDINE N-OXIDES AND N,N-DIOXIDES AND METHODS OF RESTORING, STIMULATING OR ENHANCING THE IMMUNE SYSTEM WITH THEM

[75] Inventors: Ralph G. Child; Thomas L. Fields, both of Pearl River, N.Y.; Raymond G. Wilkinson, Montvale, N.J.; Yang-I Lin, Nanuet, N.Y.

[73] Assignee: American Cyanamid Company, Stamford, Conn.

[21] Appl. No.: 669,917

[22] Filed: Nov. 9, 1984

[51] Int. Cl.$^4$ ............... A61K 31/47; C07D 219/06
[52] U.S. Cl. ............................... 514/297; 546/104
[58] Field of Search ............... 546/104; 514/297, 240, 514/239; 544/125

[56] References Cited

U.S. PATENT DOCUMENTS

| | | | |
|---|---|---|---|
| 1,727,480 | 9/1929 | Mietzsch | 546/104 |
| 2,500,131 | 3/1950 | Linsker | 546/106 |
| 3,119,809 | 1/1964 | Nicolaus | 564/299 |
| 3,592,819 | 7/1971 | Fleming et al. | 544/79 |
| 3,740,403 | 6/1973 | Murdock | 546/104 |
| 3,890,328 | 6/1975 | Palopoli et al. | 564/298 |
| 3,892,776 | 7/1975 | Hook et al. | 564/298 |
| 3,897,435 | 7/1975 | Ledochowski et al. | 546/106 |
| 4,314,061 | 2/1982 | Murdock et al. | 544/80 |
| 4,504,666 | 3/1985 | Earl et al. | 564/298 X |

FOREIGN PATENT DOCUMENTS

| | | | |
|---|---|---|---|
| 0490418 | 2/1930 | Fed. Rep. of Germany | 546/104 |
| 1458183 | 10/1966 | France | 546/106 |

OTHER PUBLICATIONS

Fieser, et al., "Advanced Organic Chemistry", Reinhold Publishing Co., New York, 1961, pp. 513–514.

Primary Examiner—Donald G. Daus
Assistant Examiner—Diana G. Rivers
Attorney, Agent, or Firm—R. P. Raymond

[57] ABSTRACT

This invention concerns novel 3,6-bis(substituted) acridine N-oxides and N,N-dioxides which are active as modulators of the immune system in warm-blooded animals.

28 Claims, No Drawings

3,6-BIS (SUBSTITUTED) ACRIDINE N-OXIDES AND N,N-DIOXIDES AND METHODS OF RESTORING, STIMULATING OR ENHANCING THE IMMUNE SYSTEM WITH THEM

BACKGROUND OF THE INVENTION

1. Field of the Invention:

This invention is concerned with new compounds of the formula:

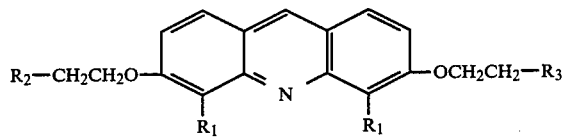

wherein $R_1$ is selected from the group consisting of hydrogen, halogen, hydroxymethyl, formyl, —COOH and alkyl-($C_1$–$C_3$); $R_2$ and $R_3$ may be the same or different and are selected from the group consisting of

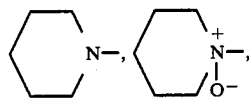

—N-[alkyl($C_1$–$C_4$)]$_2$ and

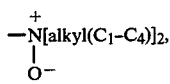

with the proviso that at least one of $R_2$ and $R_3$ must be in the N-oxide form, together with the pharmaceutically acceptable salts thereof.

In addition, the current invention is concerned with a method of treating the immune response system in a warm-blooded animal which comprises administering to said animal an effective amount of a compound selected from the compounds described hereinabove in association with a pharmaceutically acceptable carrier, adjuvant or diluent.

2. Description of the Prior Art:

The use of immunomodulants and chemotherapeutic adjuvants constitutes a new therapeutic approach to the treatment of immune deficiencies and cancer and is based on the concept that there are distinctive antigens in or on most tumor cells (embryonal or transplantation antigens) that distinguish them from normal host cells. A majority of tumor immunologists favor the view that potentially malignant cells constantly arise but, because of their "foreignness", they are normally eliminated by a competent humoral and cellular immune system. Occasionally, however, tumor cells escape this immune surveillance and continue to reproduce and cancer results. The reason for the failure of the normally efficient immune surveillance mechanisms is not fully understood but it is thought that the immune system becomes less effective with increasing age. It is depressed in certain genetic immunodeficiency diseases, in various bacterial, fungal or viral infections and in patients undergoing immuno-suppressive therapy. The growth of the neoplasm itself, as well as the various therapeutic modalities designed to treat the disease, e.g., cytotoxic chemotherapy and radiation, leads to a still greater depression of host resistance and results in an increased susceptibility to both exogenous and endogenous infections and perhaps accounts for the re-initiation of tumor growth and metastasis which frequently follows treatment-induced tumor regression.

If depression of the immune system can result in the growth of malignancies, regulation of any facet of the immune response may help the host to eliminate residual cancer cells. Therefore, it is desirable to search for chemical agents (i.e., immunoregulants) capable of restoring and stimulating host immune defense mechanisms in order to overcome the deficiencies which account for susceptibility to disease and failure to eradicate the cancer. Such immunoregulating agents would likely be incapable of arresting the growth of a large tumor but their clinical utility would derive from their capacity to enhance normal immune surveillance mechanisms in patients whose tumor burden has been reduced by surgical, radiotherapeutic or chemotherapeutic methods.

Experimental studies in animals have demonstrated the antitumor potential of a number of immunoregulants including live organisms of bacillus Calmett-Guerin (BCG), heat-killed cells of *Corynebacterium parvum*, polynucleotides, and the anthelmintic drug, levamisole. These substances have been shown to stimulate cellular immunity and to produce tumor regression. Some successes have been claimed in early clinical trials with BCG against malignant melanoma and acute leukemia and with levamisole against lung cancer and breast cancer. Although the antitumor effects produced by these agents have been promising, significant therapeutic benefits have yet to be realized. Since this is a new therapeutic approach, new drugs and methods of treatment must receive careful clinical evaluation in order to reveal their full potential.

Modern research is directed to the discovery of a drug similar to, but more potent than, known immunoregulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating immunodepression common to cancer patients. This is accomplished by infecting mice with a leukemia virus which produces both leukemia and a disease-related immunodepression. Effective drugs are recognized by their ability to restore or enhance the antibody response in the experimental mice, or to inhibit tumor progression.

Certain synthetic and naturally derived compounds have the ability to induce high levels of circulating interferon. Among these are bacterial endotoxins, intact bacteria and viruses, transplantable tumor cells and a variety of high and low molecular weight synthetic compounds such as poly I:C, tilorone and pyran copolymer [W. E. Stewart, The Interferon System, Springer-Verlag, Wein, New York (1979)]. Interferon has a major regulatory function in modulating cellular and humoral immune responses. Interferon and inducers of interferon "activate" macrophages to destroy tumor and virus infected cells, stimulate populations of immune cells to secrete lymphokines, protect against lethal infection by viruses and some bacterial species and stimulate the level of natural killer lymphocyte (NK-cell) activity in animals [Herberman, R. B. and Holden, H. T., Natural Cell-Mediated Immunity, Adv. Cancer Res., 27, 305–377 (1978) and Natural Killer Cells as Antitumor Effector Cells, J. Nat. Cancer Inst., 62 (3), 441–445 (1979)]. NK-cells play a major roll in immune surveillance in that they mediate the destruction of virus infected cells and a wide variety of syngeneic, allogeneic and xenogeneic tumor cells when tested in vitro (Herberman, R. B. and Holden, H. T., vide supra). The role of NK-cells in protecting animals against virus infection appears certain. The compounds of this invention are authentic modulators of humoral and cellular immunity in mice. The compounds induce high levels of circulating interferon, restore antibody production in immuno-suppressed mice, protect against lethal virus infection and stimulate NK-cell cytotoxicity for tumor cells.

It is a further object of this invention to provide a method of treating the immune system in a warm-blooded animal with compounds of this invention. More especially, it is an object of this invention to provide a method of treating the immune system in a warm-blooded animal with compounds of this invention in association with a pharmaceutically acceptable carrier, adjuvant or diluent.

SUMMARY OF THE INVENTION

The compounds of this invention may be prepared in accordance with the following flowchart and description.

In accordance with the above flowchart, a 3,6-bis(2-chloroethoxy)acridine (1), where $R_1$ is as described hereinabove, is reacted with piperidine in a steel bomb at about 60° to about 1000° C. for about 18 to about 36 hours, giving a 3,6-bis(2-piperidinoethoxy)acridine (3) which is then dissolved in methanol, treated with excess 30% hydrogen peroxide for about 12 to about 48 hours, then with platinum catalyst to destroy the excess peroxide and is purified by dry column chromatography on silica gel using the developing system methanol:triethylamine (20:1, v/v). The length of reaction time with hydrogen peroxide is the determining factor in whether a mono-oxide (4) or dioxide (5) is produced.

Further, compounds of the formula:

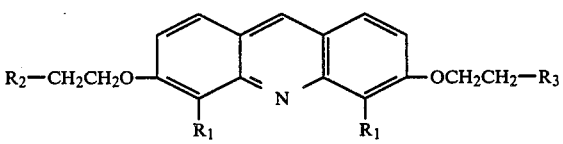

where $R_1$ is as described hereinabove and $R_2$ and $R_3$ are selected from the group consisting of —N-[alkyl($C_1$–$C_4$)]2 are dissolved in methanol, treated with excess 30% hydrogen peroxide for about 12 to about 48 hours, treated with ether and purified by recrystallization twice from acetonitrile. The length of reaction time

FLOWCHART

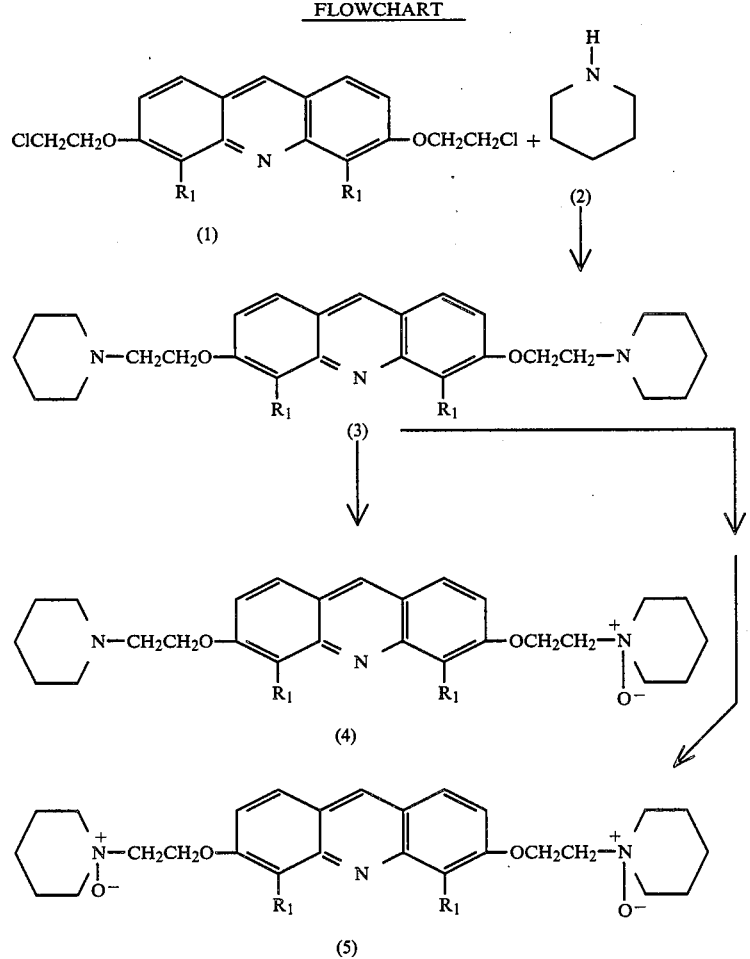

with hydrogen peroxide is the determining factor in whether a mono-oxide or dioxide is produced.

In a preferred embodiment, this invention is concerned with new compounds of the formula:

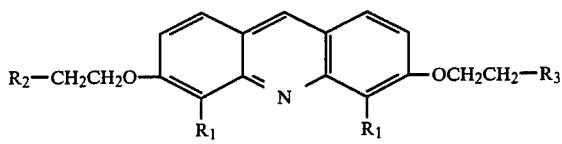

where $R_1$ is selected from the group consisting of hydrogen, chloro, hydroxymethyl, and methyl; $R_2$ and $R_3$ may be the same or different and are selected from the group consisting of:

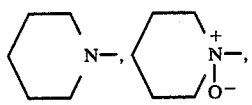

$-N(C_2H_5)_2$ and

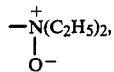

with the proviso that at least one of $R_2$ and $R_3$ must be in the N-oxide form, together with the pharmaceutically acceptable salts thereof.

In a more preferred embodiment, this invention is concerned with the following specific compounds:
3,6-bis(2-piperidinoethoxy)acridine, N,N-dioxide;
3,6-bis(2-piperidinoethoxy)acridine, N-oxide;
3,6-bis(2-piperidinoethoxy)acridine, N,N-dioxide, hydrochloride;
3,6-bis(2-diethylaminoethoxy)acridine, N,N-dioxide;
3,6-bis(2-diethylaminoethoxy)acridine, N,N-dioxide, hydrochloride;
3,6-bis(2-piperidinoethoxy)-4,5-dichloroacridine, N,N-dioxide;
3,6-bis(2-piperidinoethoxy)-4,5-dichloroacridine, N,N-dioxide, hydrochloride;
3,6-bis(2-piperidinoethoxy)-4,5-dimethylacridine, N,N-dioxide;
3,6-bis(2-piperidinoethoxy)-4,5-dimethylacridine, N,N-dioxide, hydrochloride; and
3,6-bis[2-(diethylamino)ethoxy]-4,5-acridinedimethanol, N,N-dioxide.

The compounds of the present invention have been examined in a variety of murine mode systems designed to evaluate their ability to restore or enhance cellular and humoral immune responses.

In the Rauscher virus model, the ability to produce antibodies to a complex antigen (sheep red blood cells) is severely depressed. The compounds of this invention partially restore functioning of this complex immune system and stimulate antibody production to more normal levels.

DETAILED DESCRIPTION OF THE INVENTION

The active compounds and novel compositions of the present invention are active as immune modulators when tested according to the following procedures:

(A) Inhibition of Splenomegaly and Restoration of Antibody Formation in Mice with Rauscher Virus-Induced Leukemia Injection of B ALB/c mice with Rauscher leukemia virus (RLV) is characterized by: (1) a rapidly developing viremia, (2) suppression of the primary antibody response to antigens administered a few days after virus infection, (3) a progressive enlargement of the spleen (splenomegaly), and (4) death resulting from splenic rupture and hemorrhage. The protocol used to infect BALB/c mice with RLV and to test drugs for anticancer and/or immunostimulating activity is as follows:

Day 0: Inject 0.2 ml intraperitoneally (IP) of a 20% (w/v) RLV-infected spleen cell extract into groups of 5 BALB/c mice. The spleen cell extract is prepared from mice infected with RLV 21 days previously.

Day +6, +7, +8: Test compounds are administered orally in 0.5 ml of normal saline containing 0.2% Nobel agar on days +6, +7 and +8.

Day +7: Inject 0.5 ml IP of a thrice saline washed 10% suspension of sheep red blood cells (S-RBC).

Day +14: Bleed mice from the retro-orbital sinus; pool blood from each group. Sacrifice mice, remove and weigh spleens. Serum, harvested from pooled blood of each group of mice, is stored at 4° C. for 24 hours. Hemagglutinin tests are performed by standard procedures using a microtiter technique. Acceptable hemagglutinin titer for leukemic (immunosuppressed) mice is $\leq 1:128$. The positive control compound is Poly I:C (polyinosinic acid:polycytidylic acid) administered intraperitoneally on days +6, +7 and +8. Acceptable positive control hemagglutinin titers are 4-fold higher than the titers obtained in leukemic control mice. Average spleen weights of drug treated groups of mice are compared to the average spleen weight of the RLV-infected, placebo treated mice.

Typical compounds of this invention are active in this test in that they produce a 50% or greater reduction in splenomegaly and a 4-fold or higher increase in hemagglutinin titer to sheep-RBC s relative to the placebo treated, RLV-infected control mice. Results of this test appear in Tables I and II.

TABLE I

| Rauscher Virus-Induced Leukemia-Percent Reduction in Splenomegaly | | |
|---|---|---|
| Drug Treatment | Dose (mg/kg) | % Reduction |
| 3,6-bis(2-piperidinoethoxy)acridine, N,N—dioxide | 150 | 56 |
| 3,6-bis(2-piperidinoethoxy)acridine, N—oxide | 150 | 76 |
| 3,6-bis(2-diethylaminoethoxy)acridine, N,N—dioxide | 400 | 86 |
| 3,6-bis(2-diethylaminoethoxy)acridine, N,N—dioxide, hydrochloride | 400 | 72 |
| Control | | |
| 1,4-dihydroxy-5,8-bis[[2-(2-hydroxyethylamino)ethyl]amino]anthraquinone hydrochloride(U.S. Pat. No. 4,197,249) | 100 | 82 |

TABLE II

Antibody Restoration in Mice with Rauscher Virus-Induced Leukemia

| Drug Treatment | Dose (oral) (mg/kg) | Serum Hemagglutinin Titer Saline Control Titer (Fold Increase) |
|---|---|---|
| 3,6-bis(2-piperidinoethoxy)-acridine, N,N—dioxide | 150 | 4 |
| 3,6-bis(2-piperidinoethoxy)-acridine, N—oxide | 150 | 16 |
| 3,6-bis(2-diethylamino-ethoxy)acridine, N,N—dioxide | 400 | 4 |
| 3,6-bis(2-diethylamino-ethoxy)acridine, N,N—dioxide, hydrochloride | 400 | 4 |
| 3,6-bis(2-piperidinoethoxy)-4,5-dichloroacridine, N,N—dioxide | 400 | 4 |
| 3,6-bis(2-piperidinoethoxy)-4,5-dichloroacridine, N,N—dioxide, hydrochloride | 200 | 16 |
| Poly I:C | 10(IP) | 8 |

(B) Induction of Circulating Interferon in Mice (2)

Groups of 6 normal $BDF_1$ male mice were administered a single dose of test compound by the oral, intravenous (IV), intraperitoneal (IP) or subcutaneous (SC) route. Six or eighteen hours later, mice were bled from the retro-orbital sinus and the serum from each group pooled. Control mice received a 0.3% Klucel ® (Hercules Corporation, hydroxyproplycellulose) in a normal saline placebo instead of test compound. The positive control drug for this test was Poly I:C, a recognized interferon inducer. Assays of serum interferon were carried out using the semimicroassay of W. E. Stewart (1). The interferon titer of each serum was defined as the reciprocal of the highest dilution of serum that produced a 50% reduction in cytopathic effects of vesicular stomatitis virus (VSV) on monolayers of mouse L-929 cells. The high levels of serum interferon induced in mice, following administration of test compounds, are presented in Table III below.

References to this animal model test system are:
(1) The Interferon System. Stewart, W. E. Springer-Verlag, Wein, New York, 1979.
(2) Interferon and Interferon Inducers. Stringfellow, D. A., Marcel Dekker, Inc. New York, 1980.

TABLE III

Induction of Circulating Interferon in $BDF_1$ Mice

| Compound | Dose* (mg/kg) | Route | Time After Drug Administration (Hours) | Serum** Interferon Titer |
|---|---|---|---|---|
| 0.3% Klucel ® in saline | — | oral | 18 | >100 <320 |
| 3,6-bis(2-Piperidinoethoxy)acridine, N,N—dioxide, hydrochloride | 600 | oral | 18 | 3200 |
|  | 300 | oral | 18 | 3200 |
|  | 150 | oral | 18 | 3200 |
|  | 75 | oral | 18 | 1000 |
| Poly I:C | 10 | IP | 18 | 3200 |
| 0.3% Klucel ® in saline | — | oral | 18 | >100 <320 |
| 3,6-bis(2-Diethylaminoethoxy)acridine, N,N—dioxide | 600 | oral | 18 | 1000 |
|  | 300 | oral | 18 | 1000 |
|  | 150 | oral | 18 | >1000 <3200 |
|  | 75 | oral | 18 | 1000 |
| Poly I:C | 10 | IP | 18 | 3200 |
| 0.3% Klucel ® in saline | — | oral | 18 | >100 <320 |
| 3,6-bis(2-Diethylaminoethoxy)acridine, N,N—dioxide | 600 | oral | 18 | 3200 |
|  | 300 | oral | 18 | 3200 |
|  | 150 | oral | 18 | 1000 |
|  | 75 | oral | 18 | >320 <1000 |
| Poly I:C | 10 | IP | 18 | 3200 |
| 0.3% Klucel ® in saline | — | oral | 18 | >100 <320 |
| 3,6-bis(2-Piperidinoethoxy)-4,5-dichloroacridine, N,N—dioxide | 600 | oral | 18 | 1000 |
|  | 300 | oral | 18 | 1000 |
|  | 150 | oral | 18 | <10 |
|  | 75 | oral | 18 | <10 |
| Poly I:C | 10 | IP | 18 | 3200 |
| 0.3% Klucel ® in saline | — | oral | 18 | >100 <320 |
| 3,6-bis(2-Piperidinoethoxy)-4,5-dichloroacridine, N,N—dioxide, hydrochloride | 600 | oral | 18 | 1000 |
|  | 300 | oral | 18 | 100 |
|  | 150 | oral | 18 | 10 |
|  | 75 | oral | 18 | <10 |
| Poly I:C | 10 | IP | 18 | 3200 |

*$BDF_1$ male mice received a single dose of test compound, in normal saline, at zero time.
**Reciprocal of serum dilution producing a 50% reduction in cytopathic effects of vesicular somatitis virus in murine L-929 cells.

(C) Effect of Dose Interval Time on Efficacy of Drugs Against Lethal Virus Challenge of Mice with an Interferon-Sensitive Virus, Columbia SK Swiss female mice received a single oral dose of test compound or tilorone analog [2,8-bis(N,N-dimethylglycyl)dibenzofuran, dihydrochloride (Aldrich Chem. Co.)] on the days indicated in Table IV, prior to lethal subcutaneous virus challenge on day zero with an $LD_{95}$ of Columbia SK virus. The test drugs were suspended in 1.0 ml of 0.2% aqueous agar solution. The test was evaluated 7 days after virus infection. Non-treated controls died with a mean survival time of 4.8 days after infection. The results of this test on typical compounds of this invention appear in Table IV.

The compounds of this invention are authentic modulators of humoral and cellular immunity in mice. The compounds induce high levels of circulating interferon, restore antibody production in immuno-suppressed mice, protect against lethal virus infection and stimulate NK-cell cytotoxicity for tumor cells.

It should be understood that this invention relates to modulation of the immune system in warm-blooded animals. Reference herein to animal systems using mice as test subjects is not to be construed as limiting the scope of this invention but rather as illustrative of the efficacy of the compounds of this invention.

It also should be understood that the compounds of this invention used in the above tests and the parameters of the test systems are illustrative and are not to be construed as limiting this invention.

The method of modulating the immune system of a warm-blooded animal which comprises administering to said animal an effective amount of a compound of this invention employs methods of treatment, dosage levels and requirements which are well-recognized in the art and may be chosen by those of skill in the art from available methods and techniques.

TABLE IV

Effect of Dose Interval Time on Efficacy of Drugs Against Lethal Challenge of Mice on Interferon-Sensitive Virus, Columbia SK

| Oral Treatment Time Relative to Virus Challenge (Days) | Number Survivors/Number Treated | Tilorone analog (400 mg/kg) | Non-treated Controls |
|---|---|---|---|
| | 3,6-bis(2-piperidinoethoxy)- acridine, N, N—dioxide (400 mg/kg) | | |
| −1 | 15/20* | 19/20 | 1/20 |
| | 3,6-bis(2-piperidinoethoxy)- acridine, N—oxide (400 mg/kg) | | |
| −1 | 16/20* | 19/20 | 1/20 |

*Indicates significant increase in survival ratio compared to non-treated controls (p <.01).

In order to more fully illustrate the nature of this invention and the manner of practicing same, the following examples are presented. It should be understood that the examples provided herein are illustrative and are not to be construed as limiting the scope of this invention in any way to the specific embodiments recited herein.

EXAMPLE 1

3,6-Bis(2-piperidinoethoxy)acridine, N-oxide and 3,6-Bis(2-piperidinoethoxy)acridine, N,N-dioxide A suspension of 3,6-bis(2-chloroethoxy)acridine hydrochloride in piperidine was heated in a steel bomb at 80° C. for 24 hours. The excess piperidine was removed in vacuo and the residual solution was washed twice with 30 ml portions of saturated aqueous sodium bicarbonate, then dried and filtered. The filtrate was evaporated to a residue, giving 3,6-bis(2-piperidinoethoxy)acridine as yellow crystals, mp 129°–130° C.

A solution of 4.33 g of 3,6-bis(2-piperidinoethoxy)acridine in 50 ml of methanol was treated with 2.3 g of 30% hydrogen peroxide and stirred for 24 hours. At 2 and again at 4 hours, 2.3 g of 30% hydrogen peroxide were added. At the end of 24 hours the reaction was treated with 100 mg of platinum catalyst to destroy the excess hydrogen peroxide. The mixture was filtered and the filtrate concentrated to a yellow gum. This gum was separated into two components by dry column chromatography on a silica gel column developed with methanol:triethylamine (20:1,v/v). The portion of the column containing the Rf 0.06 component was cut out, slurried with methanol, filtered, concentrated to dryness and crystallized from 20 ml of hot water and 100 ml of dioxane, giving 0.53 g of 3,6-bis(2-piperidinoethoxy)acridine, N,N-dioxide as pale yellow crystals, mp 188°–190° C.

The portion containing the Rf 0.24 component was cut out, slurried with methanol, filtered, concentrated to dryness and crystallized from 20 ml of methanol and 100 ml of water, giving 0.40 g of 3,6-bis(2-piperidinoethoxy)acridine, N-oxide as colorless crystal, mp 99°–100° C.

A repeat of the above reaction for 48 rather than 24 hours produced 3.73 g of 3,6-bis(2-piperidinoethoxy)acridine, N,N-oxide which was crystallized from 30 ml of water and 150 ml of dioxane, giving 1.65 g as pale yellow crystals, mp 188°–190° C.

EXAMPLE 2

3,6-Bis(2-piperidinoethoxy)acridine, N,N-dioxide, hydrochloride

A solution of 5.37 g of 3,6-bis(2-piperidinoethoxy)acridine, N,N-dioxide in 100 ml of 50° C. water was treated with 3 ml of 5N hydrochloric acid, stirred, treated with 400 ml of dioxane and then cooled rapidly. The resulting precipitate was recovered by filtration, washed with dioxane and dried, giving 5.18 g of the desired product as yellow crystals, mp 155° C. (dec.).

EXAMPLE 3

3,6-Bis(2-diethylaminoethoxy)acridine, N,N-dioxide

A solution of 12.3 g of 3,6-bis(2-diethylaminoethoxy)acridine free base in 120 ml of methanol was treated with 12 ml of 30% hydrogen peroxide. After 16 hours another 12 ml of 30% hydrogen peroxide was added and then at the end of 24 hours reaction time the solution was treated with 600 ml of ether giving 13 g of crude product. This material was recrystallized twice from acetonitrile, giving 9.05 g of the desired product as a pale yellow solid, mp 94°–95° C.

EXAMPLE 4

3,6-Bis(2-diethylaminoethoxy)acridine, N,N-dioxide, hydrochloride

A 4.41 g portion of 3,6-bis(2-diethylaminoethoxy)acridine, N,N-dioxide was reacted as described in Example 2, giving 5.02 g of the desired product as yellow crystals, mp 70°–72° C.

EXAMPLE 5

3,6-Bis(2-piperidinoethoxy)-4,5-dichloroacridine, N,N-dioxide 3,6-Bis(2-piperidinoethoxy)acridine was dissolved in concentrated sulfuric acid. This solution was cooled in an ice bath and N-chlorosuccinimide was added. The mixture was stirred at 0° C. for one hour then at room temperature for 18 hours, poured into ice water and the pH adjusted to 12 with 10N sodium hydroxide. The mixture was extracted with dichloromethane giving a crude material which was crystallized from hexane, giving 3,6-bis(2-piperidinoethoxy)-4,5-dichloroacridine.

A solution of 9.2 g of 3,6-bis(2-piperidinoethoxy)-4,5-dichloroacridine in 2.5 liters of n-propanol at 60° C., was treated with 75 ml of 30% hydrogen peroxide, with stirring and allowed to cool overnight. Additional 75 ml portions of 30% hydrogen peroxide were added at 24 and 48 hours and the reaction was allowed to proceed for a total of 4 days. The reaction solution was then concentrated to 900 ml and cooled, yielding 7.4 g of crude product. This material was crystallized from 75 ml of water and 400 ml of acetonitrile, giving 2.43 g of the desired product as bright yellow crystals, mp 173°–174° C.

EXAMPLE 6

3,6-Bis(2-piperidinoethoxy)-4,5-dichloroacridine, N,N-dioxide, hydrochloride

A 3.04 g portion of 3,6-bis(2-piperidinoethoxy)-4,5-dichloroacridine, N,N-dioxide was reacted as described in Example 2, giving 3.05 g of the desired product as an orange solid, mp 182°–184° C.

EXAMPLE 7

3,6-Bis(2-piperidinoethoxy)-4,5-dimethylacridine, N,N-dioxide 3,6-Diamino-4,5-dimethylacridine is prepared according to the procedure of Albert, A. and Magrath, D., J. Soc. Chem. Ind., 64, 30 (1945), from 2,6-diaminotoluene, anhydrous formic acid, zinc chloride, glycerol and hydrochloric acid.

3,6-Dihydroxy-4,5-dimethylacridine is prepared by the procedure of Benda, L., Ber., 45, 1787 (1912), for the preparation of 3,6-dihydroxyacridine from 3,6-diaminoacridine. In this reaction 3,6-diamino-4,5-dimethylacridine is heated in a bomb with two parts of water and one part concentrated sulfuric acid at 200° C. for 8 hours. The reaction mixture is diluted with water and the crude solid collected by filtration. This material is purified by dissolution in excess 1N sodium hydroxide, followed by treatment with charcoal and then acidification with acetic acid, giving an orange solid.

A 0.1 mole portion of this 3,6-dihydroxy-4,5-dimethylacridine in 300 ml of dimethylformamide is reacted with 0.11 mole of 50% sodium hydride, with stirring, under nitrogen. After 3 hours, 0.2 mole of N-(2-chloroethyl)piperidine hydrochloride is added in portions allowing the temperature to rise to 65° C. The mixture is stirred at room temperature under nitrogen overnight, then filtered and the filtrate concentrated to a residue. This residue is extracted with a mixture of water and methylene chloride. The organic layer is concentrated to an oil which is purified by dissolving in hexane and passing through a short column of alumina. The product is obtained as a yellow crystalline solid, which is 3,6-bis(2-piperidinoethoxy)-4,5-dimethylacridine.

A 4.61 g portion of 3,6-bis(2-piperidinoethoxy)-4,5-dimethylacridine in n-propanol solution is reacted as described in Example 5 with excess hydrogen peroxide, giving the desired product as a yellow solid.

EXAMPLE 8

3,6-Bis(2-piperidinoethoxy)-4,5-dimethylacridine, N,N-dioxide, hydrochloride

A 4.93 g portion of 3,6-bis(2-piperidinoethoxy)-4,5-dimethylacridine, N,N-dioxide is reacted as described in Example 2, giving the desired product as a yellow-orange solid.

EXAMPLE 9

3,6-Bis[2-(diethylamino)ethoxy]-4,5-acridine dimethanol, N,N-dioxide, hexahydrate To a solution of 0.477 g of 3,6-bis[2-(diethylamino)ethoxy]-4,5-acridine dimethanol in 12 ml of methanol was added 1.0 ml of 30% hydrogen peroxide. The mixture was allowed to stand 24 hours, then 0.5 ml of 30% hydrogen peroxide was added. After standing an additional 16 hours, 50 ml of ether was added giving 0.555 g of the desired product as yellow crystals, mp 166°–167° C.

We claim:

1. A compound of the formula:

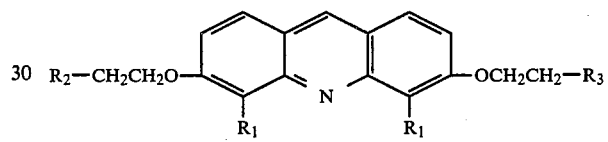

wherein $R_1$ is selected from the group consisting of hydrogen, halogen, hydroxymethyl, formyl, —COOH and alkyl-($C_1$–$C_3$); $R_2$ and $R_3$ may be the same or different and are selected from the group consisting of

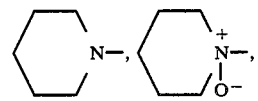

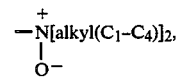

with the proviso that at least one of $R_2$ and $R_3$ must be in the N-oxide form, and the pharmaceutically acceptable salts thereof.

2. A compound of the formula:

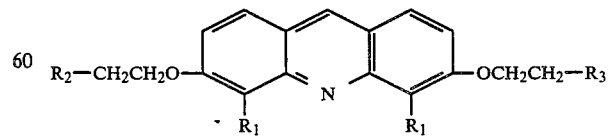

wherein $R_1$ is selected from the group consisting of hydrogen, chloro, hydroxymethyl, and methyl; $R_2$ and $R_3$ may be the same or different and are selected from the group consisting of,

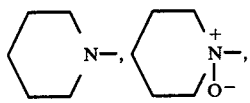

—N(C₂H₅)₂ and

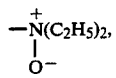

with the proviso that at least one of $R_2$ and $R_3$ must be in the N-oxide form, and the pharmaceutically acceptable salts thereof.

3. The compound according to claim 1 or 2, 3,6-bis(2-piperidinoethoxy)acridine, N,N-dioxide.

4. The compound according to claim 1 or 2, 3,6-bis(2-piperidinoethoxy)acridine, N-oxide.

5. The compound according to claim 1 or 2, 3,6-bis(2-piperidinoethoxy)acridine, N,N-dioxide, hydrochloride.

6. The compound according to claim 1 or 2, 3,6-bis(2-diethylaminoethoxy)acridine, N,N-dioxide.

7. The compound according to claim 1 or 2, 3,6-bis(2-diethylaminoethoxy)acridine, N,N-dioxide, hydrochloride.

8. The compound according to claim 1 or 2, 3,6-bis(2-piperidinoethoxy)-4,5-dichloroacridine, N,N-dioxide.

9. The compound according to claim 1 or 2, 3,6-bis(2-piperidinoethoxy)-4,5-dichloroacridine, N,N-dioxide, hydrochloride.

10. The compound according to claim 1 or 2, 3,6-bis(2-piperidinoethoxy)-4,5-dimethylacridine, N,N-dioxide.

11. The compound according to claim 1 or 2, 3,6-bis(2-piperidinoethoxy)-4,5-dimethylacridine, N,N-dioxide, hydrochloride.

12. The compound according to claim 1 or 2, 3,6-bis[2-(diethylamino)ethoxy]-4,5-acridine dimethanol, N,N-dioxide.

13. A method of restoring, stimulating or enhancing the immune system in a warm-blooded animal which comprises administering to said animal an effective amount of a compound of the formula as recited in claim 1 and the pharmaceutically acceptable salts thereof.

14. A method of restoring, stimulating or enhancing the immune system in a warm-blooded animal which comprises administering to said animal an effective amount of a compound of the formula as recited in claim 1 and the pharmaceutically acceptable salts thereof in association with a pharmaceutically acceptable carrier, adjuvant or diluent.

15. A method of restoring, stimulating or enhancing the immune system in a warm-blooded animal which comprises administering to said animal an effective amount of a compound of the formula as recited in claim 2 and the pharmaceutically acceptable salts thereof.

16. A method of restoring, stimulating or enhancing the immune system in a warm-blooded animal which comprises administering to said animal an effective amount of a compound of the formula as recited in claim 2 and the pharmaceutically acceptable salts thereof in association with a pharmaceutically acceptable carrier, adjuvant or diluent.

17. The method of restoring, stimulating or enhancing the immune system in a warm blooded animal as recited in claim 13, 14, 15 or 16, wherein the compound is 3,6-bis(2-piperidinoethoxy)acridine, N,N-dioxide.

18. The method of restoring, stimulating or enhancing the immune system in a warm-blooded animal as recited in claim 13, 14, 15 or 16, wherein the compound is 3,6-bis(2-piperidinoethoxy)acridine, N-oxide.

19. The method of restoring, stimulating or enhancing the immune system in a warm-blooded animal as recited in claim 13, 14, 15 or 16, wherein the compound is 3,6-bis(2-piperidinoethoxy)acridine, N,N-dioxide, hydrochloride.

20. The method of restoring, stimulating or enhancing the immune system in a warm-blooded animal as recited in claim 13, 14, 15 or 16, wherein the compound is 3,6-bis(2-diethylaminoethoxy)acridine, N,N-dioxide.

21. The method of restoring, stimulating or enhancing the immune system in a warm-blooded animal as recited in claim 13, 14, 15 or 16, wherein the compound is 3,6-bis(2-diethylaminoethoxy)acridine, N,N-dioxide, hydrochloride.

22. The method of restoring, stimulating or enhancing the immune system in a warm-blooded animal as recited in claim 13, 14, 15 or 16, wherein the compound is 3,6-bis(2-piperidinoethoxy)-4,5-dichloroacridine, N,N-dioxide.

23. The method of restoring, stimulating or enhancing the immune system in a warm-blooded animal as recited in claim 13, 14, 15 or 16, wherein the compound is 3,6-bis(2-piperidinoethoxy)-4,5-dichloroacridine, N,N-dioxide, hydrochloride.

24. The method of restoring, stimulating or enhancing the immune system in a warm-blooded animal as recited in claim 13, 14, 15 or 16, wherein the compound is 3,6-bis(2-piperidinoethoxy)-4,5-dimethylacridine, N,N-dioxide.

25. The method of restoring, stimulating or enhancing the immune system in a warm-blooded animal as recited in claim 13, 14, 15 or 16, wherein the compound is 3,6-bis(piperidinoethoxy)-4,5-dimethylacridine, N,N-dioxide, hydrochloride.

26. The method of restoring, stimulating or enhancing the immune system in a warm-blooded animal as recited in claim 13, 14, 15 or 16, wherein the compound is 3,6-bis[2-(diethylamino)ethyoxy]-4,5-acridine dimethanol, N,N-dioxide.

27. An immunoenhancing method which comprises administering a compound as claimed in claim 1 in an effective amount to a warm-blooded animal having an immunity-associated disease.

28. An immunoenhancing method which comprises administering a compound as claimed in claim 1 in association with a pharmaceutically accepted carrier, adjuvant or diluent in an effective amount to a warm-blooded animal having an immunity-associated disease.

* * * * *